United States Patent [19]
Zerda et al.

[11] Patent Number: 4,897,549
[45] Date of Patent: Jan. 30, 1990

[54] METHOD OF MEASURING PORE DIAMETERS BY POSITRONIUM DECAY

[76] Inventors: Tadeusz W. Zerda; Bruce Miller; C. A. Quarles, all of TCU Physics Department, P.O. Box 32915, Fort Worth, Tex. 76129

[21] Appl. No.: 286,269
[22] Filed: Dec. 19, 1988
[51] Int. Cl.$^4$ .......................................... G01N 23/00
[52] U.S. Cl. ................................ 250/358.1; 250/308; 250/393
[58] Field of Search ..................... 250/393, 358.1, 308

[56] References Cited

U.S. PATENT DOCUMENTS

| | | |
|---|---|---|
| 2,437,935 | 3/1948 | Brunner et al. |
| 3,154,773 | 10/1964 | Meile et al. ........................ 250/381 |
| 3,435,217 | 3/1969 | Givens . |
| 3,593,025 | 7/1971 | Grosskreutz .................... 250/358.1 |
| 4,463,263 | 7/1984 | Padawer ............................. 250/308 |
| 4,700,067 | 10/1987 | Carossi et al. ...................... 250/304 |
| 4,835,390 | 5/1989 | Blatchley et al. ................ 250/358.1 |

*Primary Examiner*—Carolyn E. Fields
*Attorney, Agent, or Firm*—Charles D. Gunter, Jr.

[57] ABSTRACT

A method is shown for measuring naturally occurring pores in a specimen material. A positron is emitted from a radioactive source and enters a material to pick up an electron to form positronium. The positronium decays very rapidly into two gamma rays. The lifetime of the positronium depends on the size of the pore it is trapped within. The larger the pore, the longer the positronium will last. By measuring the decay rate of positrons over an extended time scale in the range from 30 to 500 nsec., a near relation can be developed between positronium lifetime and pore diameter.

4 Claims, 5 Drawing Sheets

METHOD OF MEASURING PORE DIAMETERS BY POSITRONIUM DECAY

BACKGROUND OF THE INVENTION

1. Field of the Invention.

The present invention relates generally to pore size measurement and specifically to a method for determining pore diameters by the technique of positronium annihilation.

2. Description of the Prior Art.

Pore volume and pore surface measurements are used in the evaluation of physical properties of various materials. For instance, this information is used by chemists to study catalytic properties of reactants or additives; by geologists to predict the amount of fluids or gases trapped within the pores inside subterranean formations or to evaluate how much water is wasted by soaking into the ground of water reservoirs. Material scientists use pore volume and pore surface measurements to estimate the strength, thermal expansion, conductivity, and other properties of polymers, composites and amorphous materials.

At the present time, only the BET technique has been commonly used to study pore sizes. This technique is expensive, requires long sessions in use and has poor accuracy for pores smaller than about 40 Angstrom in diameter. Typically, the error in this region exceeds 100%. Recently, great efforts have been expended to improve the BET method and to develop an alternative technique. For example, electron microscopy, X-ray scattering and NMR on hydrogen have been used to evaluate pore sizes and pore distribution in different materials, but none has been accepted as a universal tool.

A need exists for a nondestructive testing method for determining pore sizes smaller than about 40 Angstrom in diameter with greater precision.

Another need exists for such a method for determining the pore sizes of naturally occurring pores in the range from 5 to 300 Angstroms in a specimen material which is less expensive than presently available techniques and which requires shorter sessions to run.

SUMMARY OF THE INVENTION

In the method of the invention, a source of positron radiation is provided. Positrons from the source are directed into a selected zone of a specimen material and the timing of the application of the positrons to the selected zone is sensed. The annihilation of positrons introduced into the selected zone of the specimen material is sensed and the time delay is measured between the time of application of each positron to the selected zone and the annihilation thereof. From this information, a decay rate can be determined which is characteristic of the specimen material. Each time delay is measured over a substantial time scale, the time scale for determining each time delay being in the range from about 0 to 500 nsec. The pore diameters of the specimen material are then determined as a function of the decay rate. Preferably, the pore diameters are determined by describing the decay rate as an exponential function.

Additional objects, features and advantages will be apparent in the written description which follows.

DETAILED DESCRIPTION OF THE INVENTION

Figure 1:
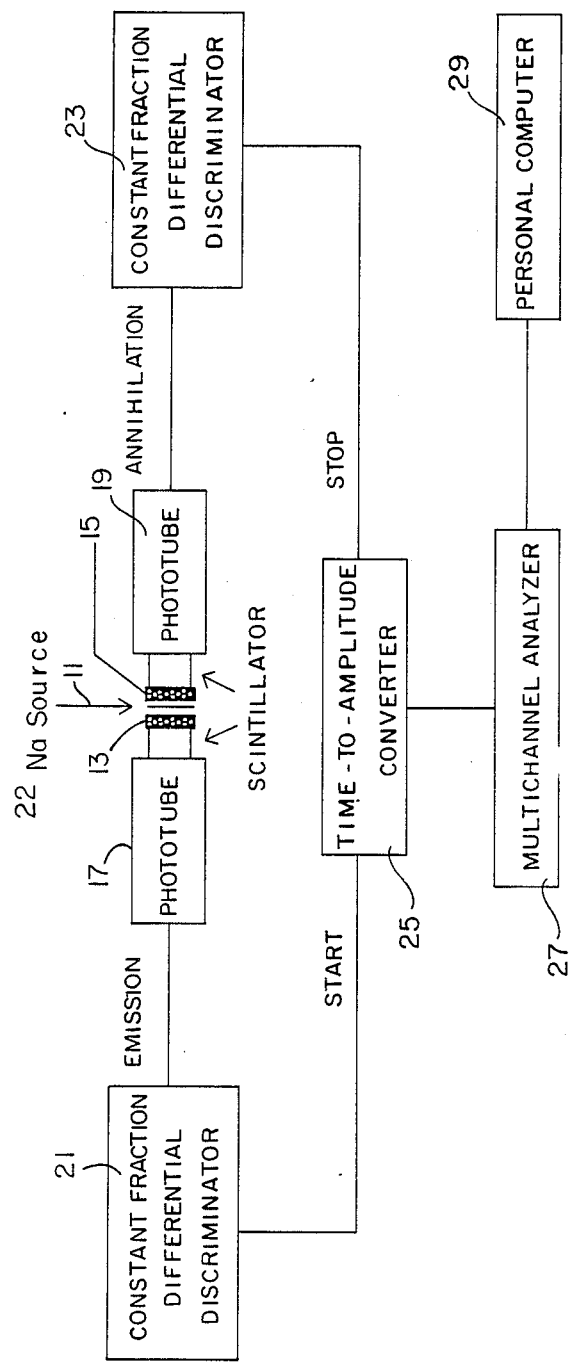
FIG. 1 is a block diagram and diagrammatic illustration of the apparatus used for practicing the method of the present invention.

The method of the invention uses the technique of positronium annihilation to measure pore diameters in a specimen material. The technique is especially well adapted to measure naturally occurring pore diameters in the range from about 5 to 300 Angstroms in a specimen material. The technique of positronium annihilation is well known. When a positron enters a specimen material, it decreases in speed very rapidly and then seeks out an electron in the material with which it combines. This combination of positive and negative charge results in complete annihilation of both the positron and the electron and the creation of two or three gamma rays. The more common two gamma ray annihilation produces two gamma rays each having an energy of approximately 0.51 Mev. As a result, the end of the lifetime of an individual positron is evidenced by the radiation of a unique energy. With knowledge of the time of entry of the positron into the material, the time duration of existence of the positron in the material before decay thereof may be ascertained to provide data for half-life computations.

In certain nondestructive testing techniques using positronium annihilation to detect crystalline defects and fatigue cracks, it has been found that the half-life of positrons is longer in materials containing dislocations and vacancies. Theoretically, it is believed that the positrons which are trapped within surface voids, such as those caused by crystal defects, require a longer time for the positron to seek out and combine with an available electron. U.S. Pat. No. 3,593,025 to Grosskreutz, issued July 13, 1971, uses such a positronium annihilation technique to search for microscopic defects, such as those caused by vacancies in the crystalline structure. The technique is not used to measure pore diameter and tracks the time delay between positron application and positron annihilation over a very short time scale, i.e. less than 30 nsec.

We have discovered that pore diameter measurements for much larger, naturally occurring pores (on the order of 5 to 300 Angstroms) can be determined by tracking the time delay between the time of application of positrons and the annihilation thereof in a specimen material over a much longer time scale, i.e. 0 to 500 nsec. In addition to tracking the time delay over a much longer time scale, the time delay measurements are analyzed over the time scale from about 30 to 500 nsec. to determine pore diameter of the specimen material as a function of the decay rate. Preferably, the pore diameters are determined by describing the decay rate as an exponential function. The invention can best be described with reference to the accompanying drawings and with reference to a particular application for pore size measurement.

The present technique is particularly well suited for measuring pore diameters in silica sol-gels of the type used in glass manufacture. A common feature of silica sol-gels is that they consist of silica particles of colloidal size, ranging from 1 to 100 nm in diameter. These particles form a rigid, continuous three dimensional network with large pores between the particles. The pores provide the necessary channels through which solvents may escape during the drying process. When the pores are wide, the solvents may leave the gel without breaking the structure. To successfully produce glasses free of cracks, strong bonds between the particles are required and pores should be of large diameter and homogeneous in size. Typically, the pore diameters increase with pH. However, the pH cannot be indefinitely increased because it also affects the size of the particles. At pH higher than 8, silica particles are large and the degree of coalescence is smaller, as a result the gels are weak and easily break. Therefore, sol-gels are usually prepared at low pH values but in the presence of chemical additives, such as formamide, glycerol, oxalic acid and fluorine salts. Also, the gels are sometimes aged at elevated temperatures, or they can undergo supercritical drying. These procedures make strong interparticle bonds and wide pores. To develop a method of making glasses using these procedures, it is necessary to control the development of pores.

Different techniques have been used in the past to measure the pore diameters of silica sol-gels. The most popular technique at the present time is the BET method which accurately measures pore diameters larger than about 40 Angstrom. However, this technique is expensive and time consuming. Low angle X-ray scattering, measurements of the volume of the imbibed liquid, mercury porosimetry, ion exclusion and electron microscopy also have been used to characterize the pore diameters of silica sol-gels.

FIG. 1 is a block diagram which illustrates the apparatus used in the method of the present invention to measure pore diameter of silica sol-gels. In the positronium annihilation technique of the invention, a source of positron radiation is provided and positrons are directed from the source into a selected zone of the specimen material. As previously mentioned, the theory of positronium annihilation is well known in the art. Thus, when a positron enters a condensed medium, such as a silica gel, it may annihilate directly with an electron, or it may capture an electron to form a hydrogen like atom, called positronium. Positronium can exist in two forms, orthopositronium, o-Ps, and parapositronium, p-Ps. Both forms decay spontaneously by direct annihilation but on very different time scales. The p-Ps form decays in a time on the order of 0.1 nsec, while o-Ps lasts longer and in a vacuum annihilates after about 140 nsec. The lifetime of o-Ps depends on its interactions with surrounding molecules and in dense systems it may be as short as 1 nsec. The shortening of the lifetime is called pick-off quenching and is caused by interactions with unpaired molecular electrons. Chemical reactions can also lead to shorter lifetimes by the so called chemical quenching process.

Referring again to FIG. 1, a housing (not shown) can be used to contain a positron source 11 in the form of a disc of a suitable radioactive substance, such as sodium 22. The radioactive source 11 is sandwiched between two specimens of the sample material 13, 15 and a scintillation counter is disposed on either side of the specimen materials 13, 15. The positrons are directed from the source 11 into the specimen material to a depth of approximately 1 mm. Phototubes 17, 19 are provided to detect the characteristic energy emission which accompanies the positron decay. Constant fraction differential discriminators 21, 23 are set to pass signals corresponding to the prompt gamma ray emission (1.3 Mev) and the two gamma ray annihilation energies (0.51 Mev), respectively. The signals received by the constant fraction differential discriminators 21, 23 are passed to a time-to-amplitude converter 25 and are then analyzed by a multichannel analyzer 27. Each spectrum is measured for 1 to 8 hours to accumulate a sufficient number of pulses.

The data is analyzed in a computer 29 after background correction to remove background noise. The background correction is performed by approximating the accidental coincidence of energy emissions of the type which would accompany positron decay. Thus, energy emissions are measured over a time scale longer than 500 nsec and before any positron annihilation from the positron source 11. By subtracting the data thus collected from the data collected during positron annihilation in the presence of the positron source 11, we were able to approximate signals only due to positron annihilation. Prior to the measurements, the samples 13, 15 are carefully dried to avoid water absorbed on the silica surfaces. Unless the samples are dried, the positronium will decay quickly through the pick-off interaction with water.

The exact circuitry used to sense the timing of the application of the positrons to the selected zone of the specimen and to sense the annihilation of the positrons and measure the time delay between the time of application and the annihilation is known in the art. For instance, such circuitry is described in U.S. Pat. No. 3,593,025, Grosskreutz, issued July 13, 1971, the disclosure of which is incorporated herein by reference. Briefly, the scintillation counters which are disposed on either side of the radioactive source 11 deliver output to a preamplifier. Both of the counters may be of the type employing a plastic scintillator in conjunction with a photomultiplier tube. The preamplifier separately amplifies each of the outputs from the respective counters 17, 19 feeds the amplified outputs to the constant fraction discriminators 21 and 23 which select the energy of the photon. The outputs of the constant fraction discriminators are then delivered to the time-to-amplitude converter 25. The time-to-amplitude converter 25 measures the time difference between the arrival of pulses from the scintillation counters 17, 19. The command pulse from the output circuit is produced if the input pulses to the circuit from the preamplifier are sufficiently coincident to be in the time scale from about 0 to 500 nsec. Therefore, if the time delay between a given prompt pulse and the corresponding two gamma ray emission is on the time scale of 0 to 500 nsec., the time-to-amplitude converter is activated to measure the length of the delay in terms of the time interval between the leading edges of the two pulses.

When activated, the time-to-amplitude converter delivers an output pulse having an amplitude proportional to the mentioned time interval between the two signals fed thereto by the pulse shapers. The output pulses from the time-to-amplitude converter 25 are fed to a pulse height analyzer which then sorts the pulses in accordance with their amplitudes. The pulse height analyzer has multiple storage channels, each corresponding to a particular time interval, to permit the accumulation of counts corresponding to the various time delays encountered.

Figure 2:
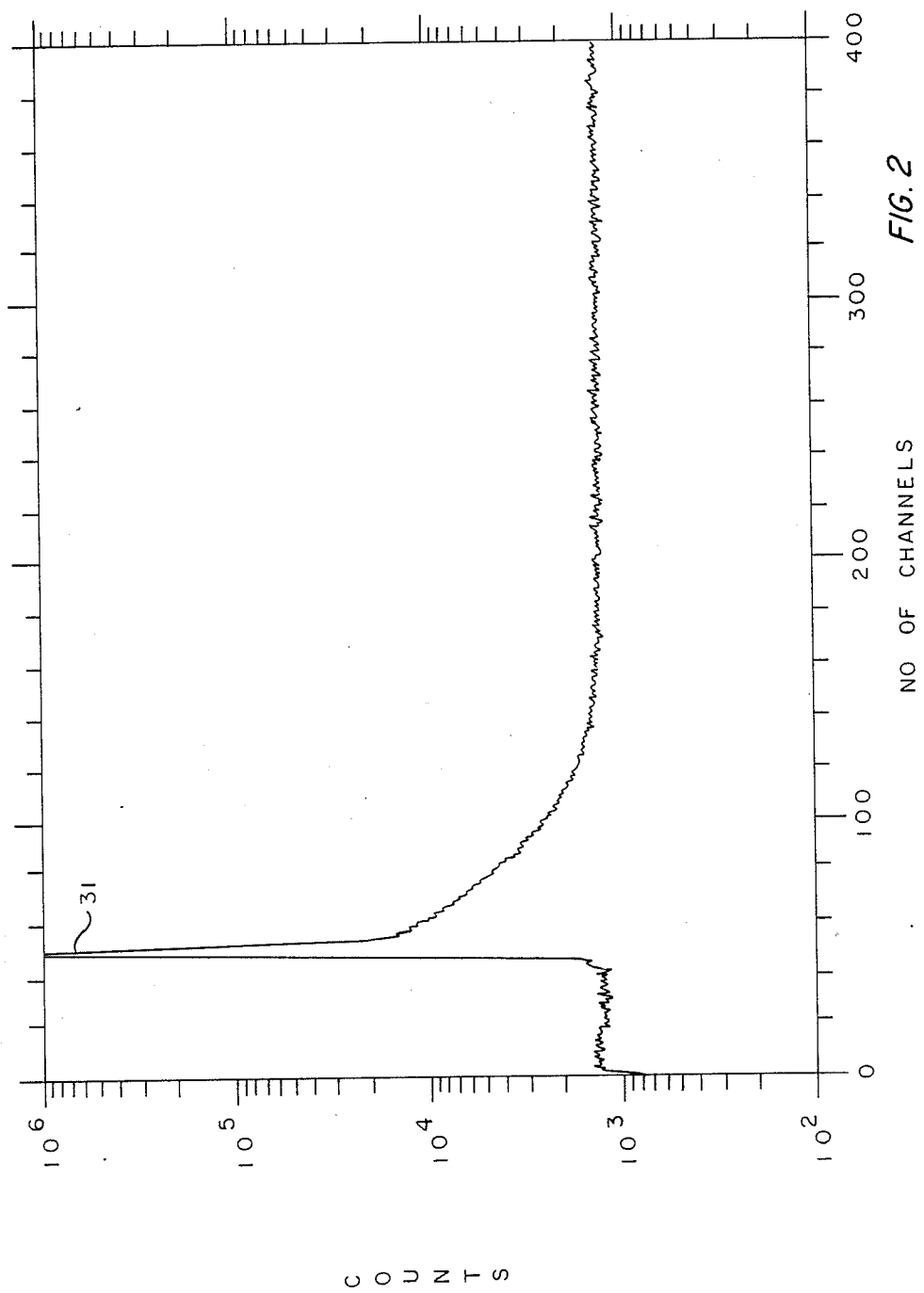
FIG. 2 is a plot of the decay rate of a specimen material obtained by the method of the present invention illustrated as an X-Y coordinate system with the number of counts plotted as ordinate against time delay as the abscissa and showing the characteristic prompt peak.

Direct readout from the pulse height analyzer 27 may be effected or the memory thereof may be fed to a digital computer 29 for conversion into information appropriate for delivery to an automatic plotter. The display of the automatic plotter is illustrated in FIG. 2 in an X-Y coordinate system wherein the number of counts from the multichannel analyzer is plotted as ordinate against time delay as the abscissa (1 channel=0.078 nsec.). The characteristic prompt peak 31 can be noted.

Figure 3:
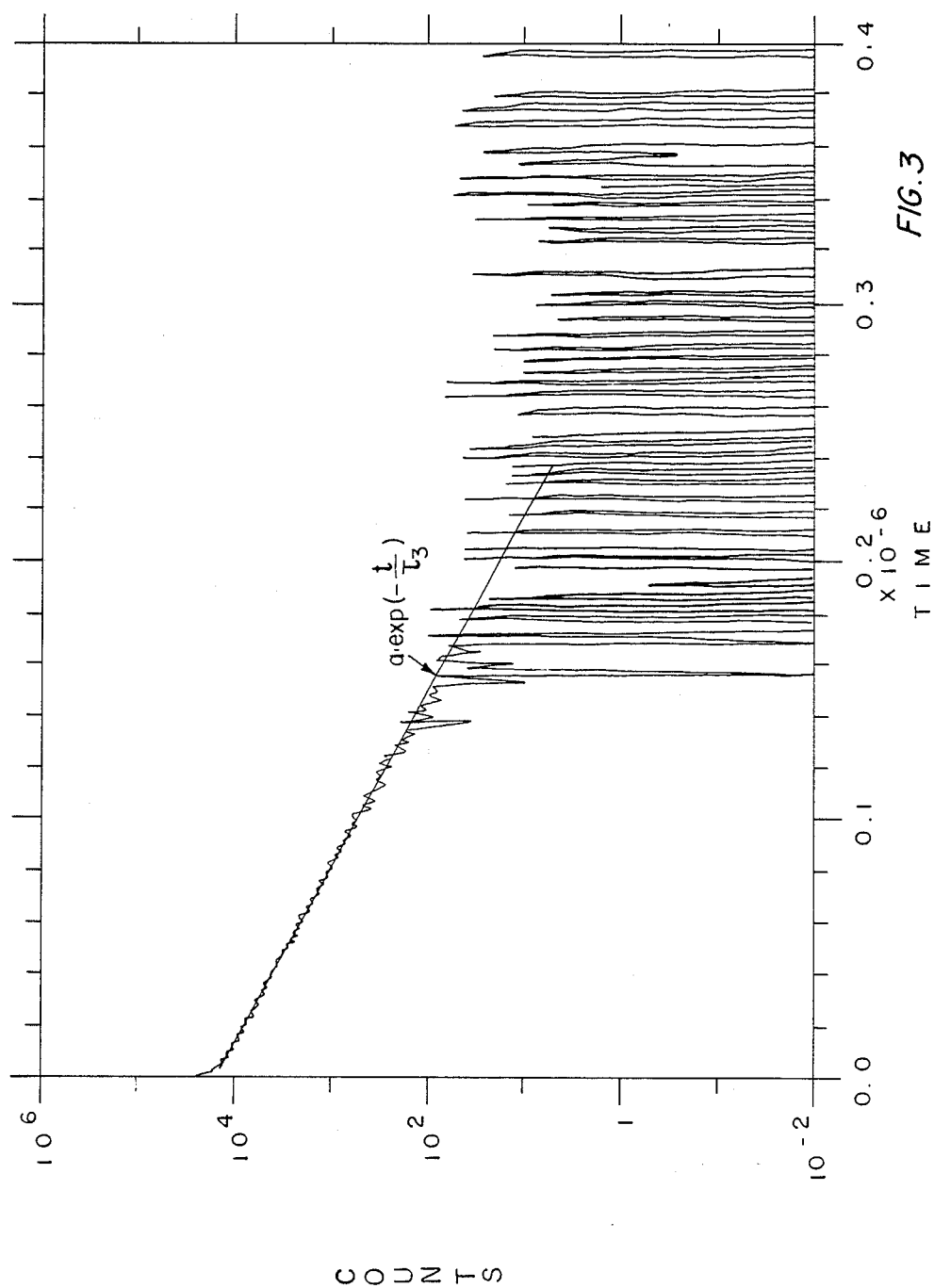
FIG. 3 is a similar plot showing the same information as FIG. 2 but with the background subtracted and the time axis originating from the center of the prompt peak.
Figure 4:
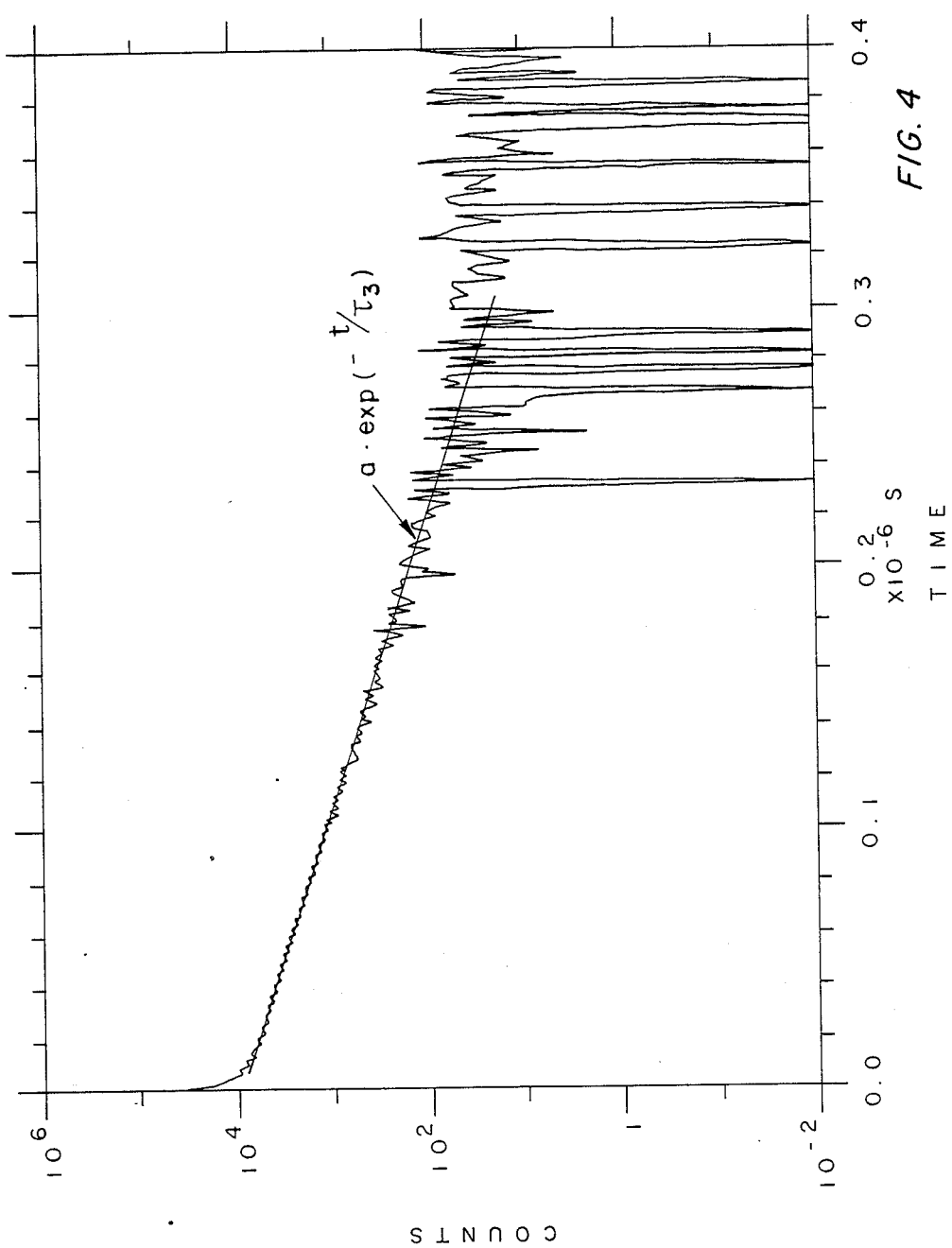
FIG. 4 is similar to FIG. 3 but shows the positronium decay plot from another sample with a different pore diameter.

FIG. 3 shows the same spectrum but with the background noise subtracted and the time axis originating from the center of the prompt peak. The o-Ps decay times were measured by the semilogarithmic slope method using as the exponential function:

$$a \cdot \exp(-\tau/\tau_3)$$

The time decay was analyzed in the range between about 20 nsec and 500 nsec, most preferably 30 to 300 nsec. In the range 0–30 nsec., all the changes in the shape of the decay curve may be attributed to unspecified chemical interactions on the surface, and as such, they cannot be used to measure pore diameters. For the particular spectrum shown, the best fit to the exponential function was found to be $a = 0.1419_{10}{}^5$ and $\tau_3 = 31.3_{10}{}^{-9}$ s.

FIG. 3 shows another positronium decay spectrum for another sample with a very different pore diameter ($\tau_3 = 49.8$ nsec.).

Figure 5:
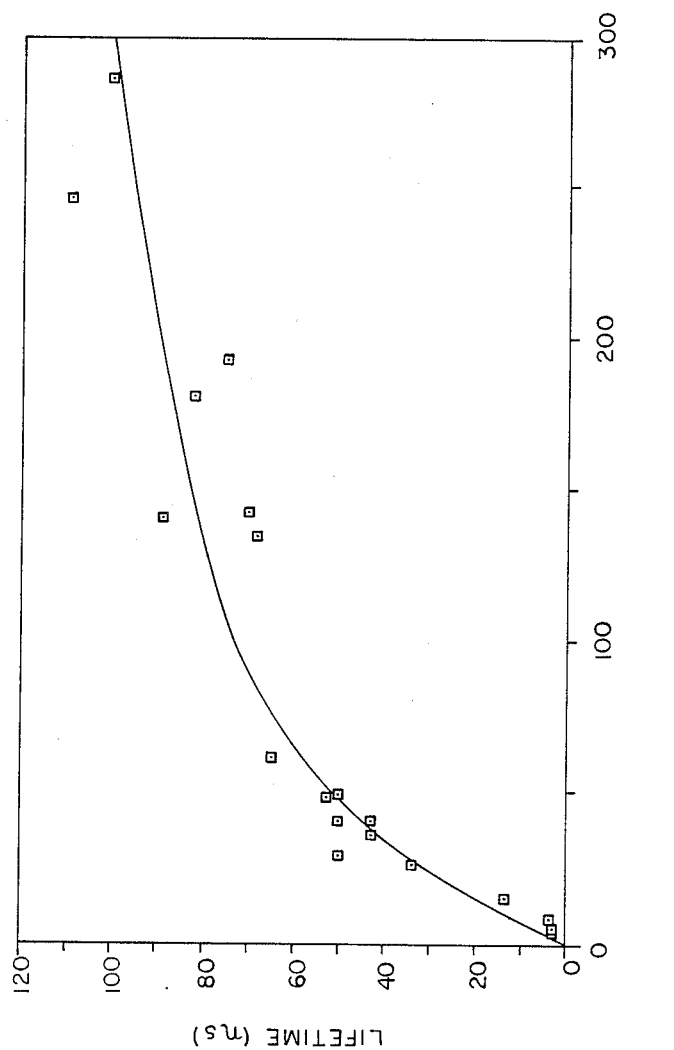
FIG. 5 is a plot showing the relationship between positronium lifetime and pore diameter determined by the method of the invention.

FIG. 5 is a graph of experimental data for samples of known pore sizes, with positronium lifetime being plotted versus pore diameter. An almost linear dependence is noted between pores diameters and positronium lifetimes. For comparison, the theoretical dependence of positronium lifetime in a spherical pore is also depicted.

The technique discussed above is very useful for measuring the average pore size of a sample with a narrow distribution of pore diameters. It is important to realize that the position annihilation technique can be extended to samples of a broad range of pore sizes. Under these circumstances, one obtains the distribution of decay rates which can then be used to obtain the pore size distribution from a deconvolution method. In addition, by comparing the results with the decay spectrum of a reference spectrum, one can find pore volume and surface area of the pores.

An invention has been provided with several advantages. Positronium annihilation has been shown to be a useful tool for analyzing pore sizes, particularly in naturally occurring, larger diameter pores such as those found in silica sol-gels. This nondestructive technique can be used to monitor pore development during the production process of glasses. Reliable results can be obtained within 1–5 hours. The instrumentation is less expensive than currently available techniques.

While the invention has been shown in only one of its forms, it is not thus limited but is susceptible to various changes and modifications without departing from the spirit thereof.

I claim:

1. A method for measuring pore diameters in a specimen material, comprising the steps of:
   providing a source of positron radiation;
   directing positrons from said source into a selected zone of said specimen material;
   sensing the timing of the application of the positrons to said selected zone;
   sensing the annihilation of the positrons introduced into the selected zone of the specimen material;
   measuring the time delay between the time of application of each positron to said selected zone and the annihilation thereof to obtain a decay rate characteristic of the specimen material, each time delay being measured over a substantial time scale, the time scale for determining each time delay being in the range from about 30 to 500 nsec.;
   determining the pore diameters of the specimen material as a function of the decay rate; and
   wherein the positrons directed from the source into the selected zone of the specimen material are directed to a depth of approximately 1 mm.

2. A method for measuring naturally occurring pore diameters in the range from 5 to 300 Angstroms in a specimen material, comprising the steps of:
   providing a source of positron radiation;
   directing positrons from said source into a selected zone of said specimen material;
   sensing the timing of the application of the positrons to said selected zone;
   sensing the annihilation of the positrons introduced into the selected zone of the specimen material;
   measuring the time delay between the time of application of each positron to said selected zone and the annihilation thereof to obtain a decay rate characteristic of the specimen material, each time delay being measured over a substantial time scale, the time scale for determining each time delay being in the range from about 30 to 500 nsec.; and
   determining the pore diameters of the specimen material by fitting the decay rate so measured to an exponential function.

3. The method of measuring pore diameters of claim 2, wherein each positron applied to the selected zone of the specimen material has a characteristic prompt peak which accompanies the emission of gamma radiation of a known energy, and wherein the pore diameters are determined as a function of the decay rate taken with the time axis originating at the center of the prompt peak.

4. The method of measuring pore diameters of claim 3, further comprising the step of subtracting background emissions from the measurements of the time delay between the time of application of each positron to said selected zone and the annihilation thereof.

* * * * *